United States Patent
Reid et al.

(10) Patent No.: US 9,834,750 B2
(45) Date of Patent: Dec. 5, 2017

(54) CELL-TO-CELL COMMUNICATION WITHOUT EXCHANGE OF MEDIATING DIFFUSIBLE FACTORS OR USING ANY PHYSICAL CONTACT BETWEEN CELLS

(71) Applicants: Christopher B. Reid, Los Angeles, CA (US); Keith Norris, Marina Del Rey, CA (US); Taehoon Cho, Los Angeles, CA (US); Victor Chaban, Los Angeles, CA (US)

(72) Inventors: Christopher B. Reid, Los Angeles, CA (US); Keith Norris, Marina Del Rey, CA (US); Taehoon Cho, Los Angeles, CA (US); Victor Chaban, Los Angeles, CA (US)

(*) Notice: Subject to any disclaimer, the term of this patent is extended or adjusted under 35 U.S.C. 154(b) by 95 days.

(21) Appl. No.: 14/764,222

(22) PCT Filed: Jan. 29, 2014

(86) PCT No.: PCT/US2014/013479
§ 371 (c)(1),
(2) Date: Jul. 29, 2015

(87) PCT Pub. No.: WO2014/120706
PCT Pub. Date: Aug. 7, 2014

(65) Prior Publication Data
US 2015/0361394 A1    Dec. 17, 2015

Related U.S. Application Data

(60) Provisional application No. 61/849,588, filed on Jan. 30, 2013.

(51) Int. Cl.
*C12N 5/0793*    (2010.01)
*G01N 33/50*    (2006.01)

(52) U.S. Cl.
CPC ....... *C12N 5/0619* (2013.01); *G01N 33/5002* (2013.01); *C12N 2502/30* (2013.01)

(58) Field of Classification Search
None
See application file for complete search history.

(56) References Cited

FOREIGN PATENT DOCUMENTS

WO    2014120706 A1    8/2014

OTHER PUBLICATIONS

U.S. Appl. No. 61/849,588, filed Aug. 7, 2014, Reid, Christopher, B. et al.
Chaban et al. "Physically disconnected non-diffusible cell-to-cell communication between neuroblastoma SH-SY5Y and DRG primary sensory neurons", Am J Transl Res, Jan. 21, 2013, p. 69-79, vol. 5, ISSN:1943-8141/AJTR1210003—the whole document.
Rosenthal et al. "Cell patterning chip for controlling the stem cell microenvironment", Biomaterials, Mar. 27, 2007, p. 3208-3216, vol. 28—the whole document.
Zaga-Clevellina et al. "Tissue-specific human beta-defensins (HBD)-1, HBD-2 and HBD-3 secretion profile from human amniochorionic membranes stimulated with Candida albicans in a two-compartment tissue culture system", Reproductive Biology and Endocrinology, Sep. 3, 2012, p. 1-11, vol. 10—the whole document.
Kanagasabapathi et al. "Dual-compartment neurofluidic system for electrophysiological measurements in physically segregated and functionally connected neuronal cell culture", Frontiers in Neuroengineering, Oct. 19, 2011, p. 1-11, vol. 4, Iss. 13—the whole document.

*Primary Examiner* — Thane Underdahl

(57) ABSTRACT

The present invention departs from using traditional modes of cell-to-cell communication and concerns exerting influence on a first cell or cell population by bringing a second cell or cell population into proximity with the first cell population without the use of mediating diffusible factors. Cell to cell communications traditionally occur by way of a variety of mechanisms including, for example, by direct coupling through gap junctions using antigen presentation or using ligand receptor interactions.

1 Claim, No Drawings

CELL-TO-CELL COMMUNICATION WITHOUT EXCHANGE OF MEDIATING DIFFUSIBLE FACTORS OR USING ANY PHYSICAL CONTACT BETWEEN CELLS

BACKGROUND OF THE INVENTION

Cell to cell communications traditionally occur by way of a variety of mechanisms including, for example, by direct coupling through gap junctions using antigen presentation or using ligand receptor interactions. Likewise, cell to cell communications can occur over very short distances (paracrine and synaptic) or very long distances by hormonal influence. However, these traditional modes of cell to cell communication require either physical contact between cells or contact with mediating diffusible factors.

SUMMARY OF THE INVENTION

The present invention departs from using traditional modes of cell-to-cell communication and concerns exerting influence on a first cell or cell population by bringing a second cell or cell population into proximity with the first cell population without the use of mediating diffusible factors. To assess the ability of cells to influence one another and cause one another to exhibit different behaviors without having any direct or indirect physical contact, either directly cell-to-cell in contact or indirectly by cell to mediating diffusible factor to cell, cultured dorsal root ganglion (DRG) cells were chosen as a test cell population. Calcium currents were then invoked in the DRG cells in response to ATP and capsaicin in the presence or absence of estradiol. Other DRG cell, cancer cells and dying DRG were chosen for cell culture in proximity as a second cell culture to influence the behavior of the test DRG cells.

An object of this invention was to determine whether physically disconnected neuro-hormonal independent non-diffusible influence occurs among cells in close proximity. Demonstration of such influence would require the ability to determine the presence of cell signaling pathways exhibiting the aforementioned cell-to-cell influence. The following sets of influencing cells were employed: human neuroblastoma SHSY-5Y (intervention 1), DRG cells with KCL induced apoptosis (intervention 2) on 17-beta-estradiol modulation of ATP- and capsaicin-induced [Ca++] changes in physically isolated DRG neurons in primary cultures. In addition, a control consisting of nutrient medium without cells was employed to investigate the potential effect of having no cells to influence a second set of cells. Further, normal DRG cells were also used as a control.

Definitions

Physically disconnected means separated or detached material, e.g., cells being physically detached one from the other or particular groups of cells being separated from another such group of cells.

Direct coupling means a direct physical linking of two independent processes by a common intermediate, for example, one cell touching another via gap junctions, antigen presentation or ligand receptor interactions.

Diffusible factor means any biologically compatible substance that when surrounding disconnected cells would enhance some form of communication or exchange of cellular materials between said cells.

Non-diffusible signaling means cellular or tissue signaling that occurs between said physically separated cells or tissues without using any diffusible factors. Said cells or tissues are also in complete physical isolation from one another, yet one set of cells or tissues influences the other to produce a substance or set of substances which would not ordinarily be produced without said influence. For example, physically isolated cells influence dorsal root ganglion neurons to exhibit a calcium [Ca++] cell signaling response when such a response would not normally occur in the absence of those physically isolated cells.

Dish-in-dish culture means placing one or more sets of cells or tissue in separated cell culture dish wells and another set of cells or tissue into a proximally located but separated cell culture dish well, thus preventing any physical contact between the sets of cells or tissue. In one example of dish-in-dish culture a special cell culture dish having an outer or surround well surrounding a physically separated inner or center well is employed to separate the two sets of cells or tissue.

Fluorescence imaging means the use of certain fluorescent labeling and staining compounds together with a suitable fluorescence imaging instrument providing greater sensitivity for detecting certain compounds such as DNA or protein. The fluorescent labeling compound attaches to the chemical to be detected, said fluorescent compound becomes excited when exposed to a certain wavelength of light and emits fluorescence which the fluorescence imaging instrument is able to detect and to record indicating the presence or absence of the expected chemical being detected.

EXAMPLE 1

DRG tissues were obtained from C57BL/6J (Jackson Laboratory; 20 g). Upon arrival, mice were housed in microisolator caging and maintained on 12 hour light/dark cycle in a temperature controlled environment. The mice had access to food and water ad libitum for two weeks. All studies were carried out in accordance with the guidelines of the Institutional Animal Care and Use Committee (IACUC) of Charles R. Drew University of Medicine and Science and the NIH Guide for the Care and Use of Laboratory Animals.

Lumbosacral adult DRG cells (level L1-S-1) were collected under sterile technique and placed in ice cold medium Dulbecco's Modified Eagle's Medium (DMEM; Sigma-Aldrich, St. Louis, Mo.). Adhering fat and connective tissue were removed and each isolated DRG tissue was minced with sterile scissors and placed immediately in a medium consisting of 5 ml of DMDM containing 0.5 mg/ml of trypsin (Sigma Type III), 1 mg/ml of collagenase (Sigma Type IA) and 0.1 mg/ml of DNAase (Sigma Type III) and all kept at 37 degrees Centigrade for 30 minutes with agitation.

After dissociation of the ganglia soybean trypsin inhibitor (Sigma Type III) was used to terminate cell dissociation. Cell suspensions were centrifuged for one minute at 1000 rpm and the cell pellets were resuspended in DMEM supplemented with 5% fetal bovine serum (FBS), 2 mM glutamine-penicillin-streptomycin mixture, 1 ug/ml DNAase, and 5 ng/ml of NGF (Sigma).

Cells were then placed on Matrigel® (Invitrogen, Carlsbad, Calif.) coated 15-mm coverslips (Collaborative Research Co., Bedford Pa.) and kept at 37 degrees Centigrade in a 5% CO2 incubator for 24 hours, then given fresh media and maintained in primary culture until used for experimental procedures.

The human SH-SY5Y neuroblastoma cells (ATCC CRL-2266) were cultured in a medium consisting of a 1:1 mixture of ATCC-formulated Eagle's Minimum Essential Medium and Ham's F-12 medium containing 10% heat inactivated FBS, 4 mM glutamine, 100 U/mL penicillin, 100 mg/mL streptomycin and 0.25 mg/mL amphotericin B in 5% (v/v) CO2 and balanced moist air at 37 degrees Centigrade.

Adjacent culture of SH-SY5Y cells with dorsal root ganglion cells occurred as follows. A dish-in-dish system involving a physically separate outer "surround" cell culture well and a separate inner "center" cell culture well was constructed, both wells capable of being managed independently (FIG. 1).

SH-SY5Y cells were plated in the surround culture well containing 10% FBS, 4 mM glutamine, 100 U/mL penicillin, 100 mg/mL streptomycin, and 0.25 mg/mL amphotericin B in DMEM.

Mouse DRG neuron cells were seeded in the center well which medium consisted of 5% FBS, 2 mM glutamine-penicillin-streptomycin mixture, 1 ug/mL DNAase, and 5 ng/mL NGF for 24 hours at 5% CO2 and 37 degrees Centigrade. Thus, the two cell populations were co-dish-in-dish cultured, separated but adjacent to each other for 12 hours prior to assessing [Ca++]i response to chemical stimulation.

Culture of KC1 Exposed DRG Cells Juxtaposed Separately with Dorsal Root Ganglion Cells Occurred as Follows.

Normal mouse DRG was plated in the surround culture well comprising 5% FBS, 2 mM glutamine-penicillin-streptomycin mixture, 1 ug/mL DNAase and 5 ng/mL NGF for 24 hours at 5% CO2 exposed at 37 degrees Centigrade.

The center culture well contained mouse DRG neuron cells, 5% FBS, 2 mM glutamine-penicillin-streptomycin mixture, 1 ug/mL DNAase and 5 ng/M1 NGF exposed for 24 hours at 5% CO2 and 37 degrees Centigrade.

The above-described plated cell populations were co-dish-in-dish cultured for 12 hours. Subsequently, KCL (50 mM) was added to the surround culture well to induce apoptosis and cell death. After additional 12 hours the [Ca++]i response to chemical stimulation was assessed.

The Control Conditions Follow Consisting of a Culture of Normal Control Root Ganglion Cells Adjacent to DRG Cells.

To establish a control condition for assessing the effect of non-diffusible cell-to-cell communication using the dish-in-dish culture system normal mouse DRG was plated in the surround culture well wherein the medium employed comprised 5% FBS, 2 mM glutamine-penicillin-streptomycin mixture, 1 ug/mL DNAase, and 5 ng/mL NGF for 24 hours exposed in 5% CO2 at 37 degrees Centigrade.

Mouse DRG neuron cells were seeded in the center culture well which medium consisted of 5% FBS, 2 mM of glutamine-penicillin-streptomycin mixture, 1 ug/mL DNAase and 5 ng/mL NGF for 24 hours with 5% CO2 and at 37 degrees Centigrade. Cells were cultured for 12 hours prior to assessing [Ca++]i response to chemical stimulation.

Culture of normal control DRG cells juxtaposed with media containing no cells took place as follows. To establish additional control conditions for assessing the effect of non-diffusible cell-to-cell communication two additional controls were performed: 1) dish-in-dish culture of normal control DRG cells in the center culture well with DRG cell media only in the surround culture well; and 2) dish-in-dish culture of normal control DRG cells in the center culture well with human SH-SY5Y neuroblastoma cell media only in the surround culture well.

[Ca++]i fluorescence imaging was carried out. DRG neurons were loaded with fluorescent dye 5 mM Fura-2 AM (Invitrogen, Carlsbad, Calif.) for 45 minutes at 37 degrees Centigrade in HBSS supplemented with 20 mM HEPES, pH 7.4. The cover slips were mounted in an RC-26 recording chamber P-4 (Warner Instruments, Hamden, Conn.) and placed on a stage of an Olympus IX51 inverted microscope (Olympus America, Center Valley, Pa.). Observations were made at room temperature (20-23 degrees Centigrade) with a 20× UApo/340 objective. Neurons were bathed and perfused with HBSS buffer using gravity at a rate of 1-2 ml/min.

Fluorescence intensity at 505 nm with excitation at 334 nm and 380 nm were captured as digital images (sampling rates from 0.1 to 2 seconds). Regions of interest were identified within the soma from which quantitative measurements were made by re-analysis of stored image sequences using Slidebook® Digital Microscopy software. [Ca++]i was determined by ratiometric method of Fura-2 fluorescence from calibration of a series of buffered Ca++ standards. E2 was applied acutely for five minutes onto the experimental chamber.

Repeated application of drugs was achieved by superfusion into individual neurons in a rapid mixing chamber for specific intervals (100-500 ms). Thereafter, actual [Ca++]i was calculated in areas of interest in each of the neurons using the following formula:

$$[Ca++]i = K_d X (R-R_{min})/(R_{max}-R) X \beta$$

where Kd is the indicator's dissociation constant of the fluoroprobe; R is the ratio of fluorescence intensity at two different wavelengths (340/380 nm for fura-2); Rmax and Rmin are the ratios at fura-2 with saturated Ca++ and free Ca++; β is the ratio of the denominators of the minimum and maximum conditions.

Statistical analysis occurred as follows. The amplitude of [Ca++]i response represents the difference between baseline concentration and the transient peak response to drug stimulation. Differences in response to chemical stimulation were assessed by comparing [Ca++]i increases during the first stimulation with [Ca++]i increases that occurred as a result of the second stimulation.

All of the data were expressed as the mean±SEM. Statistical analysis was performed using Statistical Package for the Social Sciences 18.0 (SPSS, Chicago, Ill., USA). To assess the significance among different groups, data were analyzed with one-way ANOVA followed by Scheffe post hoc test. A p<0.05 was considered as statistically significant.

As a result, the following results occurred. DRG neurons in primary culture served as a useful system for investigating sensory physiology and putative nociceptive signaling. The DRG sensory neurons are activated and/or modulated by the activation of chemosensitive receptors such as ATP-sensitive P2X3 and capsaicin-sensitive TRPV1 on peripheral nerve terminals. The TRPV1 receptor is expressed in several areas of nervous system, but it is most highly expressed in small diameter (<25 um) and medium (<40 um) diameter DRG. TRPV1 and P2X3 expressing neurons are nociceptors suggesting that P2X3/TRPV1 receptor expression and activity might be considered as markers for a specific subtype of sensory neurons and their activation by exogenous stimuli (e.g., ATP and Capsaicin).

An examination of the effect of estradiol on ATP-induced [CA++]i in DRG neurons in the presence of physically isolated local DRG cells was accomplished as follows, using the dish-in-dish culture system. A brief 10 second application of ATP (10 uM) was accomplished by using fast superfusion which resulted in the production of equal [Ca++]i spikes emitting from DRG neurons located in the center and surround culture wells.

After a five-minute washout using HBSS additional stimulation with ATP (10 uM) induced subsequent [CA++]i transients. However, pretreatment with purinergic receptor agonist PPADS (5 uM) blocked the ATP-induced [Ca++]i transients. Similarly, ATP stimulation in a Ca++-free media in the presence of Ca++ chelator BAPTA (10 mM) eliminated [CA++]i spikes, indicating the necessity for PP2X3 receptors and extracellular Ca++. 17 β-estradiol (E2) (100 nM) by itself had no effect on basal [Ca++]i but potentially attenuated ATP-induced [Ca++]i transients.

The effect of E2 was reversible. After the initial ATP response a five-minute incubation with E2 reduced ATP-induced [Ca++]i transient from 425.86±49.5 nM to 171.17±48.9 nM (n=5, $p<0.05$). Similarly the estrogen receptor agonist ICI 182,780 (1 nM) blocked the 17 β-estradiol inhibitory effect on ATP-induced [Ca++]i transients.

The characteristics of estradiol modulation of capsaicin-induced [Ca++]i flux in DRG neurons were shown as follows. A TRPV1 agonist capsaicin was applied (3 second 100 nM) by fast superfusion and produced [Ca++]i spikes which were almost completely blocked by 100 nM capsazepine, a TRPV1-selective antagonist. Since the effect of capsaicin was not reversible, estradiol was first applied (assuming its non-reversibility on TRPV-1 receptors). The E2 by itself had no effect on basal [Ca++]i but E2 (100 nM) attenuated the peak of capsaicin-induced [Ca++]i transients from 399.21±44.5 nM to 175.01±34.8 nM (n=5, $p<0.05$).

Assessment of the effect of estradiol inhibition of ATP/capsaicin-induced calcium signaling in DRG neurons in the presence of neuroblastoma SH-SY5Y cells took place as follows. ATP capsaicin-induced [Ca++]i spikes emanating from the center culture well were compared to cells in the presence of neuroblastoma SH-SY5Y cells cultures in the surround culture well. Both ATP (10 uM) and capsaicin (100 nM) induced [Ca++]i responses were significantly reduced compared to dish-in-dish cultures where DRG cells occupied the surround culture well (193±40.6 nM and 145.90±28.84 nM, respectively, n=4).

The effect of E2 on ATP-induced P2X3-mediated [Ca++]i observed under control conditions was also abolished with neuroblastoma SH-SY5Y cells in the surround culture well. Moreover, E2 similarly attenuated capsaicin-induced TRPV1-mediated [Ca++]i flux.

The effect of ATP-induced calcium signaling in DRG neurons in the presence of local physically isolated DRG neurons exposed to KCL was investigated. In a separate set of experiments ATP-induced [Ca++]i spikes from the center culture well DRG were juxtaposed and in the presence of DRG neurons exposed to KCL (50 mM) situated in the surround culture well. As a result of such non-physical interaction ATP (10 uM)-induced [Ca++]i responses were four fold higher after initial stimulation ($p<0.001$) and significantly reduced in subsequent stimulation at ten minute intervals ($p<0.001$) in the presence of DRG cells incubated in the presence of the dying (KCL saturated).

ATP/capsaicin-induced calcium signaling [Ca++]i in DRG neurons situated in the center cell or culture well was exposed in the presence of local physically isolated media placed in the surround cell or tissue culture well used to support neuroblastoma SH-SY5y cells. No significant influence by the physically isolated media was noted and the DRG neurons responded to ATP (10 uM) and capsaicin (100 nM) application as occurred under control conditions.

The effect of ATP-induced calcium signaling in DRG neurons in the presence of local physically isolated media used (the control) was then compared to DRG neurons with the addition of KCL to induce apoptosis. ATP-induced calcium [Ca++]i spikes from DRG in the presence of the media used to support the apoptosis induced on DRG neurons by 50 mM KCL placed in the surround cell or tissue culture well. There was no detection of any influence exerted by the use of experimental media on center well DRG behavior. Center DRG neurons responded to ATP 910 uM-stimulated [Ca++]i as was observed in the control.

In summary, a dish-in-dish cell culture apparatus (in this case consisting of the center well and the surround well) was used to provide proximity between evaluated normal DRG cells and dying, cancerous, or other normal (control) neuronal cells. Calcium transients were analyzed in center well contained DRG neurons following 12 hours of adjacent cell culture with either apoptotic DRG cells, neuroblastoma cells, media from neuroblastoma cells, or control cells situated in the surround well. As a result, a controlled comparison was made concerning the influence that a specific surround well population might have had on DRG inward calcium currents displayed by cells situated in the center well.

Direct application of ATP and capsaicin to test DRG cells in the center well showed responses consistent with prior studies. [Ca++]i increased in the DRG cell population in response to ATP as well as capsaicin. Further, the ATP and capsaicin-induced [Ca++]i were reduced in the presence of Estradiol.

Surprisingly, however, ATP and capsaicin induced [Ca++]i were also reduced in the presence of apoptotic and cancerous cells when singly exposed to each at different times. The same media minus the cells, however, did not have the same inhibitory effect on [Ca++]i indicating that the cells rather than the medium itself were responsible for the aforementioned inhibitory effect.

Therefore, it appears that apoptotic cells and cancerous cells are capable of exerting a non-diffusible influence over distance on nearby but physically disconnected cells.

These findings present novel support concerning the fact that physically disconnected non-diffusible cell-to-cell signaling indeed occurs.

The effect of 17 β-estradiol on P2X3/TRPV1 under pathological conditions such as anticipated stresses may be one of the mechanisms for the sensitization of neurons to pain signals and may explain sex-differences observed in clinical studies of pain-related syndromes.

Visceral nociception and nociceptors sensitization have been shown to be regulated by P2X3 and capsaicin. Findings suggest non-visceral nociception and nociceptors sensitization may also be modulated by P2X3 and capsaicin. These findings are also consistent with the hypothesis of Ventegodt et. al. suggesting the communication of biological information at the subcellular, cellular, and supracellular levels may occur through "collective connectivity" in excitable neuron cells.

However, mechanisms of action by which changes observed in DRG receptor mediated [Ca++]i fluxes are mediated, e.g., gene expression, epigenetic modification, etc., remain to be investigated. Changes in [Ca++]i fluxes could be mediated through modification of ion and calcium related gene expression (i.e., g proteins) as reported by Xiao et al., (2002) who identified marked changes following DRG axotomy with respect to the expression of 173 genes including neuropeptides, receptors, ion channels, and signal transduction molecules.

Other forms of physically disconnected cell-to-cell communication have been described, such as a post radiation therapy "bystander effect", but this is described as representing diffusible cell-to-cell interactions whereby irradiated cells induce effects on local non-irradiated cells via gap junction communication or paracrine diffusible factors (involving a form of physical contact). Such effects of tissues or cells on more distant tissues have been termed "abscopal effects" and characterize cellular changes commonly believed to be mediated through neuronal pathways or systemic diffusible factors. The novel system that is the present invention eliminates the availability of any potential pathways for neural or diffusible factor mediated cell-to-cell communication.

The present invention also displays that the effect of the sex hormone 17 β-estradiol on both P2X3 and TRPV1 receptors in mouse DRG neurons was significantly modified in the presence of human neuroblastoma SH-SY5Y cells or DDRG undergoing KCL apoptosis through what appears to be a non-local, non-physically induced form of cell-to-cell communication as described herein.

In a preferred embodiment this invention consists of a method of inducing a certain behavior in the second cell population by bringing the first cell population into close but non-physical proximity with the second cell population for the purpose of inducing a behavior in the second cell population which is displayed only in the first cell population.

What is claimed is:

1. A method of inducing ATP-mediated and capsaicin-mediated [CA++] fluxes in a normal DRG cell population by bringing an apoptotic DRG or human neuroblastoma cell population into close proximity but non-physical contact with said first cell population for the purpose of inducing the behavior in the normal DRG cell population which is displayed in the apoptotic DRG or human neuroblastoma cell population, the method comprising the steps of:
    a. physically separating the normal DRG cell population and the apoptotic DRG or human neuroblastoma cell population by using a container consisting of two separate compartments, one compartment being a surround compartment and the second compartment being a center compartment located within said surround compartment;
    b. nourishing said normal DRG cell population and the apoptotic DRG or human neuroblastoma cell population using a medium contained within said two separate compartments;
    c. causing an ATP-mediated and capsaicin-mediated [CA++] fluxes which are displayed in the apoptotic DRG or human neuroblastoma cell population in the normal DRG cell population located in one of said compartments through the apoptotic DRG or human neuroblastoma cell population located in said second compartment without any physical exchange of media between said compartments or any physical contact between said cell populations situated in said separate compartments.

* * * * *